US011638529B2

(12) United States Patent
Vallée et al.

(10) Patent No.: US 11,638,529 B2
(45) Date of Patent: May 2, 2023

(54) SYSTEM FOR MEASURING THE MEAN ARTERIAL PRESSURE

(71) Applicant: ASSISTANCE PUBLIQUE—HOPITAUX DE PARIS, Paris (FR)

(72) Inventors: Fabrice Vallée, Paris (FR); Jona Joachim, Paris (FR); Maxime Coutrot, Paris (FR); Joaquim Mateo, Paris (FR); Étienne Gayat, Paris (FR); Alexandre Mebazaa, Paris (FR)

(73) Assignee: ASSISTANCE PUBLIQUE—HOPITAUX DE PARIS, Paris (FR)

( * ) Notice: Subject to any disclaimer, the term of this patent is extended or adjusted under 35 U.S.C. 154(b) by 103 days.

(21) Appl. No.: 16/955,251

(22) PCT Filed: Dec. 21, 2018

(86) PCT No.: PCT/EP2018/086748
§ 371 (c)(1),
(2) Date: Jun. 18, 2020

(87) PCT Pub. No.: WO2019/122406
PCT Pub. Date: Jun. 27, 2019

(65) Prior Publication Data
US 2020/0390347 A1    Dec. 17, 2020

(30) Foreign Application Priority Data

Dec. 22, 2017 (FR) ........................................ 1762978
Dec. 29, 2017 (FR) ........................................ 1763405

(51) Int. Cl.
A61B 5/021    (2006.01)
A61B 5/00     (2006.01)
A61B 5/1455   (2006.01)

(52) U.S. Cl.
CPC ........ *A61B 5/02116* (2013.01); *A61B 5/4821* (2013.01); *A61B 5/6816* (2013.01);
(Continued)

(58) Field of Classification Search
CPC .............. A61B 5/0071; A61B 5/02116; A61B 5/02416; A61B 5/14556; A61B 5/4821;
(Continued)

(56) References Cited

U.S. PATENT DOCUMENTS 5,269,310 A    12/1993  Jones et al.
5,309,916 A    5/1994   Hatschek
(Continued)

FOREIGN PATENT DOCUMENTS

FR    3024943 A1    2/2016
WO    2007128518 A1    11/2007
(Continued)

OTHER PUBLICATIONS

International Search Report and Written Opinion dated Mar. 22, 2019 for corresponding PCT Application No. PCT/EP2018/086748.
(Continued)

*Primary Examiner* — Eric F Winakur
*Assistant Examiner* — Abid A Mustansir
(74) *Attorney, Agent, or Firm* — Polsinelli PC

(57) ABSTRACT

The present invention relates in particular to the field of anesthesia and to a method for real-time evaluation of the mean arterial pressure of a patient from plethysmography measurements. It also relates to a method for treating a patient comprising by continuously evaluating the mean arterial pressure of the patient, based on values continuously calculated by plethysmography.

13 Claims, 9 Drawing Sheets

(52) U.S. Cl.
CPC ............ *A61B 5/6826* (2013.01); *A61B 5/725* (2013.01); *A61B 5/7225* (2013.01); *A61B 5/7278* (2013.01); *A61B 5/14552* (2013.01); *A61B 2505/05* (2013.01); *A61B 2560/0223* (2013.01)

(58) Field of Classification Search
CPC ................ A61B 5/6816; A61B 5/6826; A61B 5/7225; A61B 5/725; A61B 5/7278; A61B 2560/0223; A61B 5/14552; A61B 2505/05; A61B 5/02225
See application file for complete search history.

(56) References Cited

U.S. PATENT DOCUMENTS

| | | | | |
|---|---|---|---|---|
| 5,792,052 | A * | 8/1998 | Isaacson | A61B 5/6826 600/323 |
| 6,293,915 | B1 * | 9/2001 | Amano | A61B 5/721 600/501 |
| 2007/0055163 | A1 | 3/2007 | Asada et al. | |
| 2011/0009754 | A1 | 1/2011 | Wenzel et al. | |
| 2011/0270047 | A1 * | 11/2011 | O'Brien | A61B 5/0205 600/301 |
| 2012/0022384 | A1 * | 1/2012 | Teixeira | A61B 5/7203 600/509 |
| 2012/0203077 | A1 * | 8/2012 | He | A61B 5/02438 600/382 |
| 2014/0107504 | A1 * | 4/2014 | Stapelfeldt | G16H 40/63 600/485 |
| 2017/0360314 | A1 | 12/2017 | Proenca et al. | |
| 2019/0015023 | A1 * | 1/2019 | Monfre | A61B 5/14532 |

FOREIGN PATENT DOCUMENTS

| | | |
|---|---|---|
| WO | 2015181622 A1 | 12/2015 |
| WO | 2017037369 A1 | 3/2017 |

OTHER PUBLICATIONS

Eric S. Winokur et al., "A wearable vital signs monitor at the ear for continuous heart rate and Pulse Transit Time measurements," Engineering in Medicine and Biology Society, 2012, pp. 2724-2727 XP032463504.

Zachary Cohen et al., "Optical-Based Sensor Prototype for Continuous Monitoring of the Blood Pressure," IEEE Sensors Journal, vol. 17, No. 13, 2017, pp. 4258-4268 XP011652521.

M. Feissel, "The pulse oxymetry plethysmographic curve: an old signal with a great future? Principles and clinical applications," Science Direct, vol. 16, 2007, pp. 124-131.

Yassine Ghamri et al., "Automated Pulse Oximeter Waveform Analysis to Track Changes in Blood Pressure During Anesthesia Induction: A Proof-of-Concept Study," Original Clinical Research Report, vol. 130, No. 5, 2020, pp. 1222-1233.

Jona Joachim et al., "Real-time estimation of mean arterial blood pressure based on photoplethysmography dicrotic notch and perfusion index. A pilot study," Journal of Clinical Monitoring and Computing, 2020, pp. 1-10.

Frederic Michard, "Smartphones and e-tablets in perioperative medicine," Korean Journal of Anesthesiology, vol. 70, No. 5, 2017, pp. 493-499.

O. Desebbe et al., "A Novel Mobile Phone Application for Pulse Pressure Variation Monitoring Based on Feature Extraction Technology: A Method Comparison Study in a Simulated Environment," Society for Technology in Anesthesia, vol. 123, No. 1, 2016, pp. 105-113.

"Anesthesia: Beyond the Horizon," Society for Technology in Anesthesia, 2015, pp. 1-3.

AJL—Capstesia; pp. 1-2.

D. Iglesias-Posadilla et al., "Apps and intensive care medicine," Medicina Intensiva, 2017, pp. 1-10.

S. B. Shah et al., "Capstesia: The smart hemodynamic monitor!" Science Direct, 2016, pp. 1-5.

B. Barrachina et al., "Assessment of a smartphone app (Capstesia) for measuring pulse pressure variation: agreement between two methods," EJA, vol. 33, 2016, pp. 1-6.

B. B. Larraza et al., "Capstesia, a new App for advanced hemodynamic monitoring," Revista Espanola de Anestesiologia y Reanimacion, 2014, pp. 1-2.

* cited by examiner

SYSTEM FOR MEASURING THE MEAN ARTERIAL PRESSURE

CROSS-REFERENCE TO RELATED APPLICATIONS

This application is a national stage application (under 35 U.S.C. § 371) of PCT/EP2018/086748, filed Dec. 21, 2018, which claims benefit of French Application No. 1762978, filed Dec. 22, 2017, and French Application No. 1763405, filed Dec. 29, 2017, which are incorporated herein by reference in their entireties.

TECHNICAL FIELD

The present invention relates to the field of anesthesia, and more particularly to a novel procedure and a novel algorithm which can be used in particular to monitor the general condition of a patient during anesthesia and in particular during the period of induction of anesthesia.

PRIOR ART

The role of the anesthetist-resuscitator is to watch over and ensure the control of the patient's major vital functions during general anesthesia, throughout the entire duration of this anesthesia, and especially during the induction period, a critical period when the use of high doses of anesthetic to induce loss of consciousness most often leads to low arterial pressure.

This hypotension results from the interaction between the vasodilating direct peripheral effect of hypnotic and morphinomimetic drugs and the central anesthetic effect of the arterial pressure control centers. Indeed, arterial pressure (AP) is a finely regulated physiological parameter that is compensated for by complex reflex systems. During general anesthesia all these systems are globally inhibited in proportion to the depth of anesthesia. The risk associated with hypotension is demonstrated, but the threshold at which consequences for the perfusion of one or more organs appear varies according to the mechanism, the associated abnormalities (CF, cardiac output and oxygen transport) and the particular terrain of the patient.

The major role of mean arterial pressure in the perfusion of organs, especially those most susceptible to hypoperfusion (brain, heart, digestive tract and kidneys), exposes them to a risk of failure if it drops.

In clinical practice, the prevention of intraoperative arterial hypotension allowing a mean arterial pressure to be maintained close to the initial mean arterial pressure, i.e. before anesthesia, is widely practiced in order to reduce the vital risk and for the improvement of the postoperative period. In addition, vasoactive agents are used during general anesthesia in order to correct as quickly as possible any potentially deleterious variations in mean arterial pressure, in particular phenylephrine, ephedrine and norepinephrine.

Three arterial pressures can be commonly measured: systolic (SAP) and diastolic (DAP) arterial pressures are measured using an arm cuff and a stethoscope, with the doctor listening for the onset and disappearance of the pulse. These pressures represent the maximum systolic and minimum diastolic pressures, respectively, during a cardiac cycle. Mean arterial pressure (MAP) is measured with a sphygmomanometer and is indicative of the perfusion pressure of the organs.

The sphygmomanometer (or electronic electrocardioscope tensiometer) does not use the principle of the auscultatory or palpatory method, but an oscillometric measurement. When the sleeve placed on the patient's forearm deflates automatically, oscillations are recorded by the device. These oscillations start before the actual systolic value and end after the actual diastolic value. The maximum value of the oscillation represents the mean arterial pressure (FIG. 1). From this MAP value and algorithms developed by the manufacturers, the SAP and DAP are calculated. This is the device that is used by anesthetists in operating theatres.

The mean arterial pressure can be estimated from the systolic and diastolic arterial pressures by the formula $MAP = \frac{2}{3} DAP + \frac{1}{3} SAP$. However, this formula is only an estimate, discussed in the art, other formulas having been developed (see in particular Razminia et al. Catheter Cardiovasc Interv. 2004 December; 63(4):419-25). In a response given on Research Gate, Gianni Losano (University of Turin) recalls the definition of mean arterial pressure (the mean of all arterial pressure values throughout a cardiac cycle), and that it can sometimes be the mean between systolic and diastolic pressure. https://www.researchgate.net/post/What_formulas_and_methods_exist_for_the_calculation_of_mean_arterial_blood_pressure It therefore appears that the knowledge of systolic and diastolic pressures is insufficient to know the mean arterial pressure.

The anesthesiologist's goal is therefore to protect the patient from physiological disturbances induced by the surgical procedure and the anesthetic agents. It requires continuous monitoring of the cardiovascular system (heart rate, arterial pressure), the respiratory system (breathing rate, pulse oximeter, expired $CO_2$) and temperature in the case of lengthy procedures. This control must be adapted to the risks and contexts to limit these episodes of hemodynamic instability.

Routine minimum monitoring includes in particular the measurement of mean arterial pressure at least every 5 minutes, invasively or non-invasively, and the continuous measurement of arterial oxygen saturation ($SpO_2$). These controls are required by the regulations.

Non-invasive mean arterial pressure measurement is currently carried out using the oscillometric method with a cuff, as described above. However, one of the major limitations of this arterial pressure monitoring is that it is intermittent and therefore systematically lagging behind the hemodynamic variations caused by anesthesia. Thus, it is not possible to obtain continuous arterial pressure values. Indeed, the arterial pressure measurement takes about one minute and cannot be repeated too often, to prevent repeated inflation of the cuff from injuring the patient's arm.

Oxygen pulse saturation is measured by plethysmography with a sensor usually positioned at the fingertip. This measurement is inexpensive and provides continuous information.

This sensor is called a pulse oximeter (plethysmograph) and contains two red light-emitting diodes that must face a receiving area. The diodes emit two lights (red and infrared) and their absorption by the pulsating flow is measured. This absorption of red and infrared light varies depending on whether it encounters reduced non-oxygenated hemoglobin (Hb) or oxygenated oxyhemoglobin ($HbO_2$). The output data are therefore absorption data. FIG. 2 shows that the absorption measured by the pulse oximeter contains several components, with the only variable observed under steady state conditions being systolic arterial flow.

The pulse wave is generated by the heart with every beat. It causes changes in blood volume in the arteries, which contract and relax as it passes through. This wave is dicrotic, reflecting (first peak) the expulsion of blood from the ventricle into the cardiovascular system (systolic pressure), and (second peak, or change in the slope of the pulse wave decay after the maximum) the residual propulsion observed at the closure of the sigmoid valves, and representing the relaxation (contraction) of the arteries close to the heart that had dilated to absorb the influx of blood during blood propulsion.

It is also recalled that the arterial pressure wave can be described according to its mean and pulsatile components. The mean component is the MAP, which is considered constant from the aorta to the large peripheral arteries while the pulsatile component varies according to complex phenomena all along the arterial tree.

A smartphone application already exists as an aid for monitoring certain physiological parameters (Captesia, described in particular by Desebbe et al., Anesth Analg 2016; 123:105-13). This application requires taking a photograph of the pulse wave graph, as appearing by plethysmography, and sending this photograph to a server, along with certain patient parameters. The application returns the variation of the pulse pressure, but not the mean arterial pressure in real time and continuously, as it requires operator intervention. This application is linked to patent application WO 2015/181622.

Application WO 2017/037369 describes a non-invasive device for the measurement of aortic flow in a small mammal, using a device for the plethysmography of the thorax by inductance measurement, acquisition and analysis of the cross-sectional change signal of each coil.

Application FR3024943 describes a process for determining an individual's respiratory rate from heart rate by measuring the cardiac signal by plethysmography.

Application WO 2007/128518 describes a non-invasive device for continuous measurement of arterial pressure (AP) characterized in that it comprises means for indirect measurement from a signal (VS) representing directly or indirectly the variations in volume of blood in an organ or part of the body, said volume variation signal being calibrated using intermittent AP values obtained by standard non-invasive methods, preferably without using one or more predefined constants, and in particular one or more physiological parameters assumed to be constant. The signal (VS) representing directly or indirectly the variations in blood volume in an organ or part of the body may be the plethysmographic wave of the blood oxygen saturation (SpO2) measured with a saturometer on the finger, toe, ear, forehead, nostrils, or other organ or part of the body. This device may comprise means for detecting the amplitude of the signal VS and the time for which the signal VS reaches its maximum (VSmax) and/or its minimum (VSmin) and/or a predefined reference value (VSO), during each heartbeat (cycle), by calculating in real time the following parameters:

the rise time (Tm) for each heartbeat (cycle), defined as the time interval of the passage of the signal VS from the value VSmin or the value VSO to the value Vsmax during its rise: Tm=t(VSmax)–t(VSmin) or Tm=t(VSmax)–t(VSO);

and/or the descent time (Td) for each heartbeat (cycle), defined as the time interval of the passage of the signal VS from the value VSmax or the value VSO to the value VSmin during its descent: Tm=t(VSmin)–t(VSmax) or Tm=t(VSmin)–t(VSO).

However, this document only describes the evaluation of systolic arterial pressure using signal amplitude and peak rise time with one calibration per cuff. However, as mentioned, this calibration is not correct because the cuff only gives an estimate of the systolic pressure. In addition, this document does not disclose how to obtain the function linking the measured parameters on the pulse wave and the systolic pressure. Therefore, it appears that the teaching of this document is not relevant to solve the problem addressed in the present application (measurement of mean arterial pressure, which is crucial for organ perfusion) because peripheral systolic pressure is not a good indicator of tissue perfusion. In addition, systolic pressure depends very largely on where it is measured. Thus, it can be seen in FIG. 1 that the systole on plethysmography does not vary in the same way as the actual systole. It should also be noted that the equation proposed in this document uses a constant, to take into account the diastolic pressure (the calculation is performed on the pulsed pressure) and which represents more or less the volume of blood that has been pumped and rejected by the heart. The use of this constant adds to the uncertainty of the method in this document.

U.S. Pat. No. 5,269,310 describes a method of determining arterial pressure by attaching a plethysmograph to a patient such that said plethysmograph interacts with an artery of said patient, said plethysmograph generating an output signal having a predetermined relationship to a characteristic of blood in said artery; calibrating said plethysmograph during a calibration period by determining the actual arterial pressure of the patient by means other than said plethysmograph, and then determining the value of a first arterial characteristic in a predetermined relationship between said first arterial characteristic, the arterial volume indicated by said plethysmograph output signal, a conversion value corresponding to the arterial volume at infinite pressure, and said actual arterial pressure during said calibration period; and analyzing said plethysmograph output signal during a measurement period to determine an arterial pressure corresponding to said output signal in accordance with said predetermined relationship. This teaches the measurement of electrical voltages corresponding to systole and diastole (column 6) and to a calculation of an electrical voltage corresponding to the "mean electrical voltage". The methods described do not refer to obtaining or using the mean arterial pressure.

U.S. Pat. No. 5,309,916 describes a process for assessing arterial pressure, based on two variables, and essentially describes the use of pulse wave velocity and blood flow velocity.

Application US 20070055163 describes the use of a plethysmographic signal for measuring arterial pressure. The authors apply an external pressure to the patient and measure the resulting signal, allowing the system to be calibrated. However, this document does not mention that dicrotic wave measurement can be used to measure or estimate mean arterial pressure.

Application US 20110009754 relates to the calculation of arterial pressure, and mentions the measurement of various parameters. In particular, it mentions measuring the maximum of the pulse wave or the time between the start of the pulse wave and the dicrotic wave (FIG. 7.E). Thus, this paper is more interested in the arrival times of plethysmographic signals. This is explicit in paragraph [0144], which states that "The velocity of the pressure pulsation traversing the arteries is positively correlated with systolic blood pressure. Therefore, as explained above, measures of pulse arrival time (PAT), and metrics indicative of PAT, can be used to estimate arterial blood pressure". Thus, this paper does not consider measuring the dicrotic wave height, nor does it suggest that this could be of interest, despite the large number of parameters suggested.

Winokur et al. (Conf Proc IEEE Eng Med Biol Soc. 2012; 2012:2724-7) refers to a device monitoring electrocardiogram (ECG), ballistocardiogram (BCG) and photoplethysmogram (PPG) with two light sources. This document indicates that the Pulse Transit Time (PTT) extracted from the cross-correlation between PPG and BCG shows improved results compared with the pulse arrival time (PAT, considered in US 20110009754) method for monitoring changes in mean arterial pressure.

Zachary Cohen (IEEE Sensors Journal, Volume: 17, Issue: 13, Jul. 1, 2017) describes a prototype ring sensor for continuous measurement of blood pressure. This paper describes a linear correlation between the measured voltage in volts of each heartbeat and arterial pressure. This document describes the measurement of systolic and diastolic pressure.

DISCLOSURE OF THE INVENTION

The invention relates to a novel ex vivo method for continuous real-time assessment of the mean arterial pressure of a patient, particularly of a patient undergoing anesthesia, which uses values obtained in real time. Preferably, these values have been obtained by plethysmography. This method therefore enables the anesthetist to react immediately in the event of a drop in pressure below a predetermined threshold. It should be noted that the method described below is not implemented on the human body, but is carried out ex vivo, using previously measured values. The invention does not include the measurement of the values, but only their manipulation (described below) in order to obtain a reliable estimate of the patient's arterial pressure.

Thus, the methods described below are preferentially based on the measurement of the pulse wave by plethysmography, which is a consequence of the systolic expulsion, and allow the inference and monitoring of the change in mean arterial pressure, which, as mentioned above, is not clearly and directly related to the systolic arterial pressure. Measurement by plethysmography is performed using a saturometer (pulse oximeter) on the finger, toe, ear, forehead, nostrils, or other organ or part of the body. It is preferred when this measurement is made with a finger or earlobe pulse oximeter.

Since the relationship between mean pressure and systolic and diastolic pressure is complex, and since the pulse wave represents systolic pressure and is used to calculate oxygen saturation, it is surprising that the pulse wave can be used to measure overall mean pressure. Such a result could not be envisaged in view of the prior art, and it can be noted that the documents mentioned above do not mention it, even though the mean pressure is the parameter that makes sense in anesthesia to confirm a good perfusion of the organs.

The invention thus relates to a method (or a process) carried out ex vivo for continuously assessing the mean arterial pressure of a patient, based on values of a continuously measured parameter, comprising the steps:
  I. Calculate a calibration value Calib from
    a. The arterial pressure value at a time t0
    b. The value Vp0 related to the parameter measurement obtained in the patient at the time t0,
  II. Calculating the estimated value MAPest of the patient's arterial pressure at a time t after t0 by the formula MAPest=k×Calib×Vpt, wherein Vpt is the value of the parameter measurement obtained at the time t.

This method therefore provides a mean arterial pressure value at each heartbeat. This method is very favorably implemented by computer, thus in silico.

Thus, the continuous mean arterial pressure can be evaluated using the correlation coefficient Calib calculated on the basis of an actual measurement of the mean arterial pressure at the time t0 and a measurement of the physiological parameter that can be obtained continuously at the same time t0. The mean arterial pressure (at t0 or later in case of recalibration) is measured by any method known in the art (cuff or directly by intra-arterial probe). The value Calib can be recalculated from time to time, in particular at regular intervals by measuring a new arterial pressure value and measuring a new value for the parameter Vp, this new subsequently recalculated value Calib being used until the new calibration.

It is preferred when the continuously measured parameter Vp is measured by plethysmography. There are various methods of plethysmography, and the method preferred in the context of the invention is photoplethysmography or photoelectric plethysmography.

This method enables to determine the excess volume of blood at each heartbeat (perfusion index, PI) related to blood expulsion after systole. Thus, the PI is expressed as a percentage of the "non-pulsatile" blood volume of the finger.

This method also measures the ratio of deoxyhemoglobin to oxyhemoglobin (known as $SpO_2$).

The rendering of a photoplethysmography is a graph representing the variation of the measured volume, as well as the two values PI and $SpO_2$ mentioned above. This graph represents the pulse wave and reflects the blood expulsion at the time of systole. It shows the two pressure peaks that send blood into the body (main peak at the exit of the heart and secondary peak (dicrotic wave) after relaxation of the vessels near the ventricle). This dicrotic wave can be represented on the graph by a second peak, appearing during the decay observed for the main peak, by a plateau, or by a change in slope during the decay of the main peak (corresponding to the blood flow, which is too low to create a new peak or a plateau). The shape taken of this second pressure wave (dicrotic wave), at the level of the plethysmograph graph, depends on several factors, such as the nature and accuracy of the plethysmograph, the cardiac state of the patient, and/or the state of the patient's vessels. However, as mentioned above, it is always possible to detect this second pressure wave.

In a preferred embodiment, the value of the dicrotic wave is used as the value Vpt of the continuously measured parameter. The height of this dicrotic wave is used if a peak or plateau can be observed (FIGS. 4.A and 4.B). If only a break in the decay curve is observed, the location of this break is used as the start of the dicrotic wave (FIG. 4.C). The dicrotic wave height (dicrotic notch) used is very preferentially the total or absolute height of the plethysmographic signal (Hd, FIG. 3) in preference to the height measured from the baseline of the pulsatile part (which corresponds to the diastolic height). In fact, the absorption value of this baseline is likely to vary over time (FIG. 7.B), which can lead to miscalculations if the absolute value of the absorption measured at the appearance of the dicrotic wave is not taken into account.

In another embodiment, the value Vpt that can be continuously calculated is related to the logarithm of the inverse of the perfusion index (PI) at the time t.

In another embodiment, the value Vpt used is the time between the start of the pulse wave and the dicrotic wave (the slope break observed when the pulse wave decreases) designated as T2 in FIG. 3.

In another embodiment, the value Vpt used is the time from the start of the pulse wave to the maximum of the pulse wave, designated as T1 in FIG. 3.

In another embodiment, the value Vpt used is the period of the pulse wave (time measured between the feet of two successive pulse waves), designated as T3 in FIG. 3. This parameter is essentially used as a secondary parameter, when several variables are used, in particular to weight the MAPest calculated with another parameter.

In another embodiment, the value Vpt is the ratio of the value of the dicrotic wave to the value of the maximum systolic peak or the ratio of the value of the dicrotic wave to the value of the diastole (foot of the pulse wave).

As mentioned above, the pulse wave is the pressure wave that can be detected as a result of blood flow to an organ and is therefore related to heartbeat and systole.

It is very interesting to use the dicrotic wave height, which can be used to estimate the value of the MAP. However, it can be advantageous to also use the perfusion index (directly, its inverse or the logarithm of its inverse). Indeed, the perfusion index varies inversely to MAP (see the examples), i.e. it increases as MAP decreases. It can also be seen that the perfusion index is a very sensitive marker, which starts to "move" (increase) as soon as the MAP decreases, this change being earlier than the change in the dicrotic wave height. Thus, it can be envisaged to monitor both markers (dicrotic wave height and perfusion index), paying attention if the perfusion index increases (or the inverse of the perfusion index or the logarithm of the inverse decreases) and even more carefully if the increase is followed by a decrease in dicrotic wave height. Thus, the invention also relates to a method (ex vivo) of evaluating or estimating the mean arterial pressure of a patient, comprising the steps of Measuring the value of the perfusion index, in particular by photoplethysmography Evaluating the change in that index or a function of that index (such as the inverse of the index, logarithm of the inverse of the index)

Evaluating the mean arterial pressure value by a method as described below (in particular by measuring the dicrotic wave height by photoplethysmography) in the event of a change in the perfusion index (increase) or the composite variable (inverse of the index, logarithm of the inverse of the index, decrease).

The invention also relates to a method (or a process) for continuously assessing the mean arterial pressure of a patient, based on values of a continuously measured parameter, comprising the steps:

I. Measure the mean arterial pressure in a patient at a time t0

II. Measure the value of the parameter Vp0 at the time t0

III. Calculate a calibration value Calib from
  a. The arterial pressure value obtained in I at the time t0
  b. The value Vp0 obtained in II at the time t0, IV. Measure the value of the parameter Vpt at the time t after t0

V. Calculate the estimated value MAPest of the patient's arterial pressure at the time t by the formula MAPest=k×Calib×Vpt, where Vpt is the value of the parameter measurement obtained in V.

A recalibration can also be carried out from time to time (for example every 5 minutes). This recalibration consists of recalculating the value Calib on a regular basis and using this new value Calib until the next recalibration.

The invention relates to an application for treatment of a patient in need thereof, comprising the step of administering a vasopressor to the patient, when the estimated mean arterial pressure (MAPest), as calculated by the methods described in the present application, drops or falls below a predetermined threshold. This indicates that the patient is hypotensive and the administration of a therapeutically effective amount of a vasopressor (which increases a lowered arterial pressure) will restore adequate arterial pressure. Vasopressors are known in the art and include sympathomimetics (including adrenaline, dopamine, ephedrine . . . ), glucocorticoids and mineralocorticoids, angiotensinamide . . . . In hospital settings, sympathomimetics are used instead.

In a particular embodiment, the value Vpt used at the time t is an averaged value of several measured values over a predetermined time period. Using such an averaged value makes it possible to avoid any singular variation at a time t. In particular, the value averaged over three systoles can be used.

In a particular embodiment, the method described above is performed on a patient during general anesthesia. This method is therefore used for a period of several tens of minutes or even several hours. It may be advisable to recalibrate from time to time, particularly when taking arterial pressure readings from the cuff.

Thus, the method described above (actual arterial pressure measurement, measurement of the parameter, calculation of the value Calib, subsequent evaluation of the arterial pressure using this value Calib) can be repeated several times at predetermined intervals. In particular, this method can be repeated each time the cuff pressure is taken (i.e. essentially recalculating a value Calib), or every two or three times. This avoids possible drift of the estimated mean arterial pressure value between two actual measurements. This calculation of the value Calib can also be performed if the estimated mean arterial pressure value is too far (10% or 5% variation) from the actual value measured from time to time.

In another embodiment, the value MAPest evaluated at the time t can also be refined by calculating several of these values (using different continuously measurable parameters) and interpolating (evaluating) the actual value MAPest, based on the several results obtained. Thus, n individual measurements are made with n parameters (for example dicrotic waves, PI, time difference between peaks . . . ), then the estimated MAPest is measured for each of the parameters, and a final MAPest is calculated probabilistically.

Thus is described an ex vivo method for continuously assessing the mean arterial pressure in a patient, characterized in that
  a. the method described above is repeated for different parameters, in order to obtain several values MAPest at the time t (each linked to a particular parameter)
  b. a value MAPestfinal is calculated by statistical estimation taking into account
    i. the different MAPest values calculated at the time t
    ii. one or more MAPestfinal values calculated before the time t.

In step a), a MAPest can thus be calculated at the time t on the basis of the measured values of the following parameters selected from among the dicrotic wave height, the logarithm of the inverse of the perfusion index (PI) (to which 1 is added to avoid obtaining a negative value), the duration between the start of the pulse wave and the dicrotic wave, and the duration between the start of the pulse wave and the maximum of the pulse wave. Alternatively, the ratio (dicrotic wave height/maximum height of the pulse wave) and/or the ratio (dicrotic wave height/height of the diastolic part (foot of the pulse wave)) can be used.

In particular, a MAPest at the time t can be calculated on the basis of the following combinations of measured parameter values dicrotic wave height and logarithm of (the inverse of the perfusion index (PI)+1)

dicrotic wave height and duration between the start of the pulse wave and the dicrotic wave dicrotic wave height and time from pulse wave start to pulse wave maximum dicrotic wave height, logarithm of (the inverse of the perfusion index (PI)+1), and duration between the start of the pulse wave and the dicrotic wave dicrotic wave height, logarithm of (the inverse of the perfusion index (PI)+1), and time from pulse wave onset to pulse wave maximum pulse wave height, time from the start of the pulse wave to the maximum of the pulse wave, and time from the start of the pulse wave to the dicrotic wave dicrotic wave height, logarithm of (the inverse of the perfusion index (PI)+1), duration between the start of the pulse wave and the dicrotic wave, and duration between the start of the pulse wave and the maximum of the pulse wave Other combinations that do not include the height of the dicrotic wave can also be considered and/or the ratios (height of the dicrotic wave/maximum pulse wave height) and/or (height of the dicrotic wave/height of the diastolic part) can be incorporated.

It is preferred when the dicrotic wave height (or the ratio dicrotic wave height/systole height, or the ratio dicrotic wave height/systole height) is one of the variables measured and used, the other variables being selected from those mentioned above. In fact, and as shown in the examples, the parameters related to the dicrotic wave (and in particular to its height) give a very good value of the mean arterial pressure, and will essentially have the most important weight in the determination of the MAPestfinal, the other variables being essentially used to weight the variables related to the dicrotic wave, which may be of interest for some patients.

After implementation of step a), n estimated values of mean arterial pressure (n being the number of parameters selected) are obtained.

Step b) consists in assessing a mean arterial pressure based on these n estimated values and on the value estimated at the previous time.

Such an evaluation can be carried out by any statistical method known in the art, and in particular by using a Kalman filter in discrete context. The Kalman filter in discrete context is a recursive estimator. This means that to estimate the state at a time t, only the estimate of the previous state and the measurements at the time t are used. The history of observations and estimates is thus not required.

The use of multiple parameter values and statistical probability as well as filters such as the Kalman filter increases the reliability of the displayed measurement of mean arterial pressure compared with a measurement evaluated only on the basis of a single parameter. In particular, this makes it possible not to give too much weight to outliers that could be obtained for a parameter at a given time (for whatever reason).

In another embodiment, an ex vivo method is thus described for the continuous evaluation of the mean arterial pressure in a patient, characterized in that a. the method described above is repeated for different parameters (Vpnt), in order to obtain several values MAPest (MAPestn) at the time t (each linked to a particular parameter)

b. a value MAPestfinal is calculated by combining the different MAPest values calculated at the time t.

The combination described in step b) is preferably a linear regression, and the MAPestfinal is written a1MAPest1+a2 MAPpest2+ . . . (MAPestn corresponding to the MAPest value obtained for the parameter Vpnt measured at the time t).

This linear regression is performed by any method known in the art, taking into account the relative weight of the MAPestn values for each parameter. The factors a1, a2 . . . are preferentially recalculated at each actual measurement of mean cuff pressure.

Preferably, this method is used when a certain amount of data is already available, allowing the quality of the coefficients to be refined. For example, coefficients previously calculated on a cohort of other patients (at least 50, preferably at least 100 patients) can be used as initial coefficients. Indeed, even if there is inter-patient variability and the coefficients obtained on this cohort are not necessarily the best for the patient in question, these previously calculated coefficients can be used before being refined according to the data obtained for the patient. Thus, at each calibration the MAPest is calculated with the previously used coefficients (the initial coefficients (from the cohort) at the first calibration)

this value is compared with the measured MAP value coefficients are adjusted by giving increasing weight to the measured values for the patient in the regression as more MAP data measured in that patient become available.

Thus, the methods described above are based on the fact that mean arterial pressure can be measured according to parameters that can be measured continuously, preferably from a plethysmographic measurement. In particular, the dicrotic wave height (or the ratio to the total value of the systolic wave and/or the dicrotic wave) or the logarithm of the inverse of the perfusion index (increased by 1) are proportional to the mean arterial pressure. The method for obtaining the mean arterial pressure is therefore much simpler than those described in the prior art, while being reliable.

As mentioned above, the methods described are of particular interest for monitoring a patient's arterial pressure status continuously when the patient is under general anesthesia. This enables the physician to act quickly if the pressure is too low, without having to wait for the actual cuff measurement.

Thus, it is preferred when these methods are used continuously throughout the duration of a patient's general anesthesia.

In addition, and to ensure patient safety, a signal may be emitted when the MAPest value is below a pre-determined threshold (this may be considered if the mean arterial pressure is below 65 mmHg). Such a signaling step can be incorporated into a method as described above. The signal can be a graphical signal (such as a representation of the mean arterial pressure by a color code different from the conventional color code (red in case of an alert instead of green or yellow). Alternatively, the value may be displayed with different color codes on the monitoring monitor to alert the physician to a risk of hypotension.

The alert signal can also or alternatively be an audible signal (long beep or other) when the mean arterial pressure falls below a predetermined value. This also alerts the surgeon of a problem, and of the need for the anesthetist to perform the medical procedure to correct this hypotension.

The invention also relates to a computer product/program comprising program code instructions recorded on a computer-readable medium, for carrying out the steps of the methods described above, when said program is executed on a computer.

This program may also contain code instructions to display the mean arterial pressure value on a monitor. It may also include code instructions to emit a visual and/or audible signal if the estimated mean arterial pressure value is below a predetermined threshold (pre-programmed or entered by the clinician). It may also include code instructions for an actual arterial pressure measurement to be taken on the patient if the estimated value is below a predetermined value. Thus, the program can request and order an arterial pressure measurement before the prescribed time, without the intervention of a human being.

The invention also relates to a computer-readable recording medium on which is recorded a computer program comprising program code instructions for carrying out the steps of processes as described above or programs as described above.

The invention may also include a device for implementing a method as described above, comprising:
  means for receiving mean arterial pressure measurement data, in particular as taken by non-invasive method (cuff)
  means for receiving measurement data of one or more continuously measured parameters (in particular the dicrotic wave height, or the perfusion index)
  calculation means to calculate a coefficient Calib for each actual measurement of mean arterial pressure
  calculation means to calculate a mean arterial pressure at each time t as a function of the value of the parameters at that time t, in accordance with the methods described above
  means for presenting the calculated mean arterial pressure at each time t (optionally including means for alerting in the event that the calculated mean arterial pressure is below a predetermined value)
  optionally means for the automatic actuation of the device for measuring the mean arterial pressure, in the event that the calculated mean arterial pressure is below a predetermined value
  optionally means for the automatic administration of a dose of vasopressor, in the event that the calculated or estimated mean arterial pressure is below a predetermined value.

The computing means are essentially processors enabling the execution of computer products/programs as mentioned above. The means of receiving data, presenting mean arterial pressure, operating the sphygmomanometer or automatically administering a dose of vasopressor are classical means in the art.

The methods described above are of primary interest in the field of anesthesia and post-intervention monitoring room but can also be used in other fields such as resuscitation (especially hyperventilated patients), cardiology, town medicine, or emergency medicine (prehospital and interhospital). The methods and devices can also be used in sports medicine. The methods and devices can also be used to assess mean arterial pressure in stress testing of a patient.

The invention also relates to a method for analyzing a plethysmographic signal, and in particular to a method or methods for determining the foot of the pulse wave, the maximum of the pulse wave, and/or the dicrotic wave, on a plethysmography trace, by applying the methods more precisely described in the examples.

In particular, the foot of the pulse wave is determined by calculating the second derivative of the plethysmographic signal, the foot of the pulse wave corresponding to the maximum of this second derivative at the rising edge of the pulse wave. The first derivative can be weighted to focus only on the rising part of the signal (i.e. the second derivative is given a zero value when the first derivative is not positive). Alternatively, the values obtained can be squared and then integrated over floating windows of predetermined time, in particular 240 ms centered (averaged over the values 120 ms before and 120 ms after the desired point), in order to obtain a strong signal at each rising edge of the pulse wave. This signal can be compared with a threshold value. Preferably, this threshold value is adaptive in real time. The threshold value can be calculated by the formula: the integral (as calculated above) averaged over a floating window of 3 s (centered or not), and whose value is multiplied by 1.5. The peak (maximum) of the second derivative (which defines the foot of the wave) is identified in the area where the integral exceeds this threshold value.

The peak (maximum) of the pulse wave can be determined, after the foot of the pulse wave by
  splitting the signal into several time windows (in particular windows between 20 ms and 100 ms, in particular 50 ms), and
  looking at the maximum value in each time window (one advances window by window as long as higher values are found in the last time window studied).

The local maximum value (corresponding to the maximum value V found in a time window, the maximum value in the next time window being less than this value V) corresponds to the maximum of the pulse wave.

This method makes it possible to obtain
  the value of the maximum (absorbance value given by the pulse oximeter corresponding to the peak of the systolic wave)
  the time at which this maximum is reached.

The value and time of the dicrotic wave can be determined by
  obtaining the second derivative of the signal after the pulse wave maximum
  splitting the signal over predetermined time windows (between 50 ms and 300 ms, in particular 150 ms) after this pulse wave peak
  searching for the local maximum of the second derivative of the signal in each time window, in order to determine an area of interest (time window in which this local maximum of the second derivative of the signal is present)
  searching for the absolute minimum value of the first derivative of the signal in this area of interest. This search can be performed again, splitting the area of interest into time windows (between 5 ms and 15 ms, in particular 8 ms).

The point corresponding to the dicrotic wave corresponds to the point at which the absolute minimum value of the first derivative is reached. Its value (absorbance value given by the pulse oximeter), as well as the time between the foot of the pulse wave and this point, can then be measured.

EXAMPLES

Figure 1:
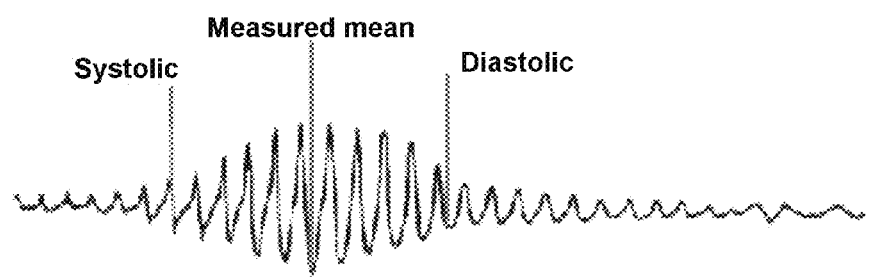
FIG. 1: Example of a graph of a sphygmomanometer signal (obtained from https://www.infirmiers.com/etudiants-en-ifsi/cou rs/cours-card iologie-la-pression-arterielle-et-sa-mesure.html)
Figure 2:
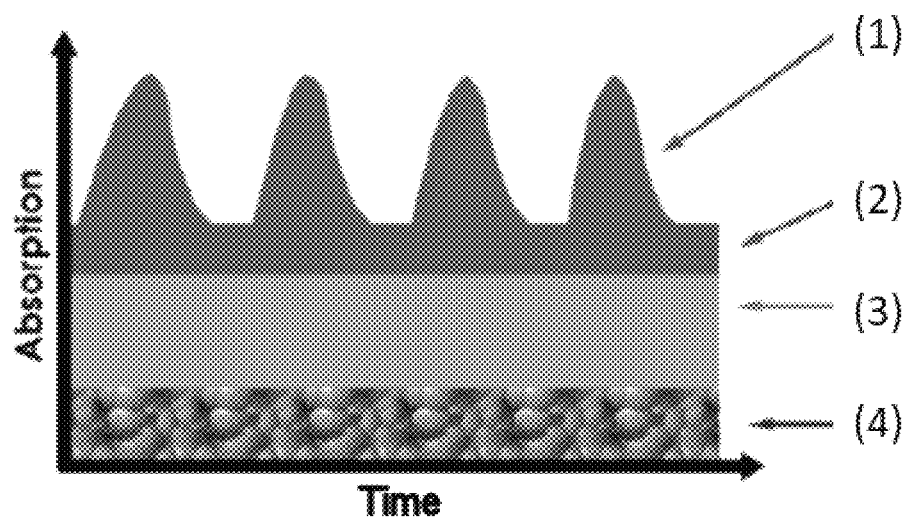
FIG. 2: Principle of pulse oximetry. (1): variable light absorption related to the variation in arterial blood volume. (2) constant light absorption related to the non-pulsatile portion of arterial blood. (3): constant light absorption related to venous blood. (4): constant light absorption related to tissue, bone, etc. According to Feissel, Réanimation 16 (2007) 124-131.

The examples below illustrate different aspects and modes of implementation of the invention. The embodiments described in the examples are an integral part of the invention.

Example 1. Determination of Parameters that can be Used for Continuous Arterial Pressure Measurement In cardiology, it is thus possible to measure the variation of the pulse wave non-invasively by plethysmography. This produces a curve (graph) representing the excess volume due to systolic expulsion.

The perfusion index (PI) reflects the amount of blood flow measured locally and in part of the pulsating arterial flow, the systolic ejection volume. The perfusion index represents the area under the curve mentioned above. In the case of photoelectric plethysmography, a value $SpO_2$ is also obtained, representing the arterial oxygen saturation.

The curve represents the profile of the pulse wave and shows the dicrotic wave at the output of the heart at systole, (a second peak (optionally two peaks), a plateau or a break in the decay) in the organ.

This plethysmographic signal can be used for continuous mean arterial pressure measurement.

Thus, variations in peak size (of the dicrotic wave), area (value of the perfusion index) or timing between two events in the pulse wave profile are used. In particular, the decay of the dicrotic wave can actually be seen, i.e. the dicrotic wave can be detected with certainty in the plethysmographic signal.

In order to determine these parameters, it is possible to analyze the pulse wave.

Foot of the Pulse Wave

First, the foot of the pulse wave can be detected. The foot of the pulse wave is characterized by a rapid rise in the signal, resulting in a peak of the second derivative of the signal. The analysis of this second derivative of the signal obtained by the plethysmograph makes it possible to obtain a signal (peak of the second derivative) at each rising edge of the pulse wave, and thus to detect the foot of the pulse wave, and thus the moment corresponding to the beginning of the signal.

Systole (Pulse Wave Peak)

From the foot of the wave, for each cycle, the maximum value of the cycle is sought. To do this, the signal can be split into several time windows and the maximum value in each time window sought. In this way the local maximum value corresponding to the maximum of the pulse wave can be determined. The result is as follows the value of the maximum (absorbance value given by the pulse oximeter corresponding to the peak of the systolic wave)

the time at which this maximum is reached

The time between the start of the pulse wave and the maximum of the pulse wave can therefore be calculated.

Dicrotic Wave

Once the peak of the pulse wave has been identified, the second derivative of the signal is analyzed over predetermined time windows (between 50 ms and 300 ms). The local maximum of the second derivative which is after the systolic peak is sought, in order to determine an area of interest in which the absolute minimum of the first derivative is searched for. The dicrotic point corresponding to the dicrotic wave corresponds to this point where the absolute minimum of the first derivative is reached. Its value (absorbance value given by the pulse oximeter), as well as the time between the foot of the pulse wave and this point, can then be measured.

Exemplification of Practical Application of this Method

Signal Collection

The signal was collected in real time from a standard patient monitor capable of providing a photoplethysmography waveform as well as non-invasive arterial pressure by means of a pressure cuff. Connection to the monitor is usually via an RS232 serial port or a network connection via ethernet or WiFi. In addition to these two essential parameters, the perfusion index (PI) value was also used. The communication with the monitor can be bidirectional and allow, for example, a new non-invasive pressure tap to be requested on demand.

Signal Analysis

The signal processing is based on an online algorithm that measures the measured values and produces a beat-by-beat result in real time.

Foot of the Pulse Wave

The software uses a heartbeat detection algorithm that relies on the detection of the foot of the pulse wave. The foot of the pulse wave is characterized by a rapid rise in the signal, resulting in a peak of the second derivative of the signal.

The detection of the foot of the pulse wave is based on the second derivative of the signal. This second derivative is weighted by the first derivative to focus only on the increasing part of the signal (i.e. the second derivative is given a zero value when the first derivative is not positive). The values obtained are squared and then float-integrated over a 240 ms centered window (averaged over values 120 ms before and 120 ms after the desired point). This integrated signal provides a powerful signal at each rising edge of the pulse wave.

This signal is compared with a threshold value. This threshold value depends on the patient, the equipment used, the shape of the plethysmographic signal and the measurement noise. Since the measurement noise is not constant, the threshold is necessarily adaptive in real time. To calculate the threshold, the integral (calculated above) is used to which a floating mean with a window of 3 s (centered or not) is applied, the result being multiplied by 1.5. The threshold thus obtained can be used to define an area of interest where the integral exceeds the threshold. Within this area of interest, the peak of the second derivative defines the foot of the wave.

Systole (Pulse Wave Peak)

From the foot of the wave, for each cycle, the detection of the dicrotic wave is done in two steps. The first step consists in finding the systole and thus the maximum value of the cycle. To do this, the signal is split into 50 ms windows and the signal is advanced window by window as long as higher values are found. Once the highest value has been exceeded, the local maximum value (corresponding to the maximum value of the pulse wave, or systole value) is found.

Dicrotic Wave

Once the peak of the pulse wave has been identified, the next step is to analyze the second derivative of the signal as it progresses through 150 ms windows. In this way the local maximum of the second derivative, which is located after the systolic peak, is sought. Once this peak has been identified, it informs of an area of interest in which the dicrotic wave is located. From this point, the first derivative is analyzed, and the absolute minimum of the first derivative is searched for within an 8 ms window from the peak of the second derivative.

The minimum of the first derivative close to the peak of the second derivative is thus obtained. This point is defined as the dicrotic point corresponding to the dicrotic wave and its value can be measured (total absorbance value given by the pulse oximeter).

Example 2. Calibration and Continuous Estimation of Mean Arterial Pressure (MAP)

Calibration requires the value (Vp) of at least one of the following parameters dicrotic wave height value of the logarithm (natural or decimal) of the inverse of the PI perfusion index (ln (1/PI+1)). 1 is added to the inverse of the perfusion index to avoid taking the logarithm of a value less than 1 and obtaining a negative result value of the time between the foot of the pulse wave and the dicrotic wave and value of the time between the foot of the pulse wave and the maximum of the pulse wave ratio "dicrotic wave height/pulse wave height" and/or "dicrotic wave height/diastole wave height".

total pulse wave duration

Figure 3:
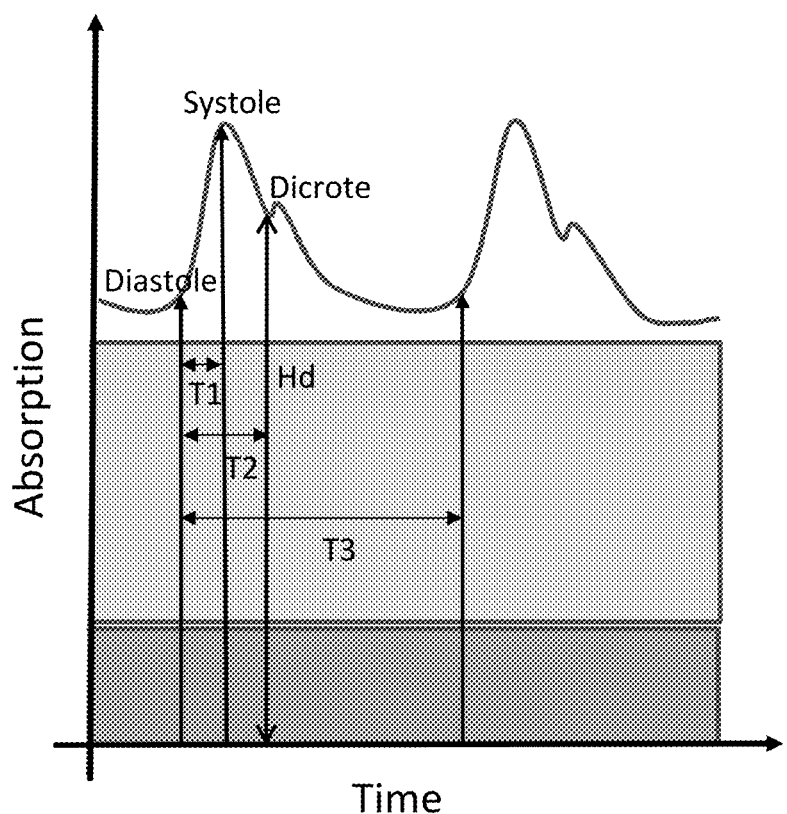
FIG. 3: Representation of the variables usable in the context of the invention, based on a pulse oximeter plot. T1: duration between the beginning and the maximum of the pulse wave; T2: duration between the beginning of the pulse wave and the dicrotic wave; T3: total duration of the pulse wave; Hd: dicrotic wave height.
Figure 4:
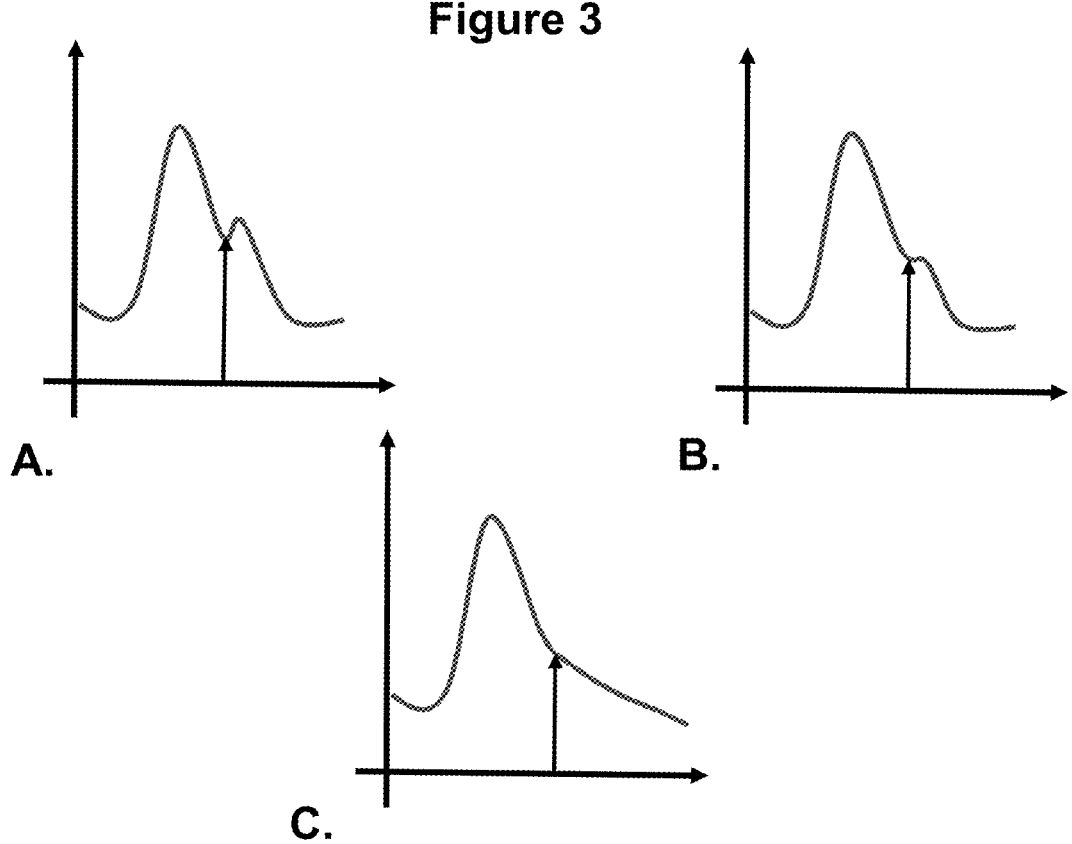
FIG. 4: Representations of different types of plethysmographic signals with dicrotic wave identification.
Figure 5:
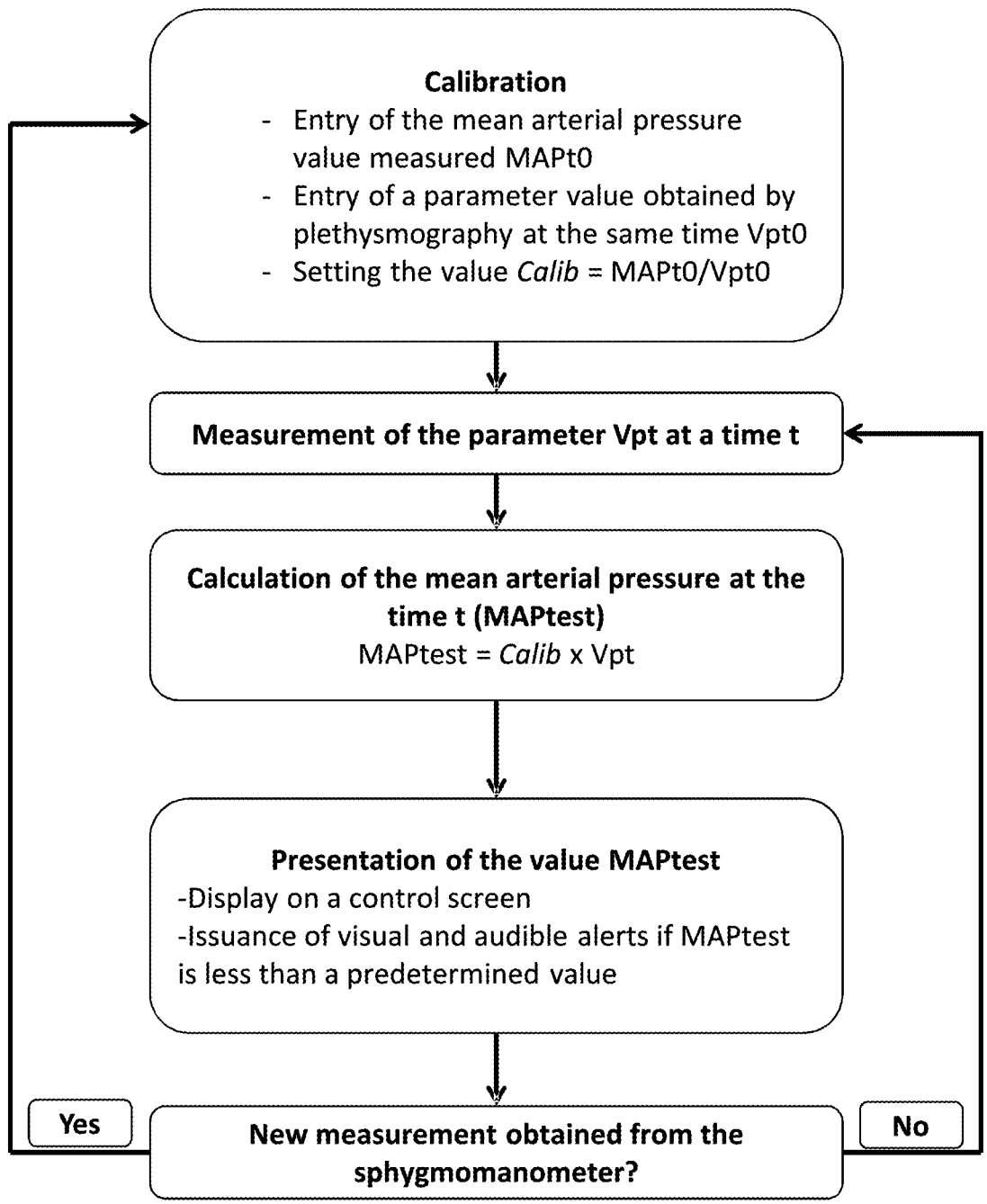
FIG. 5: Flowchart representing the implementation of a process according to the invention.
Figure 6:
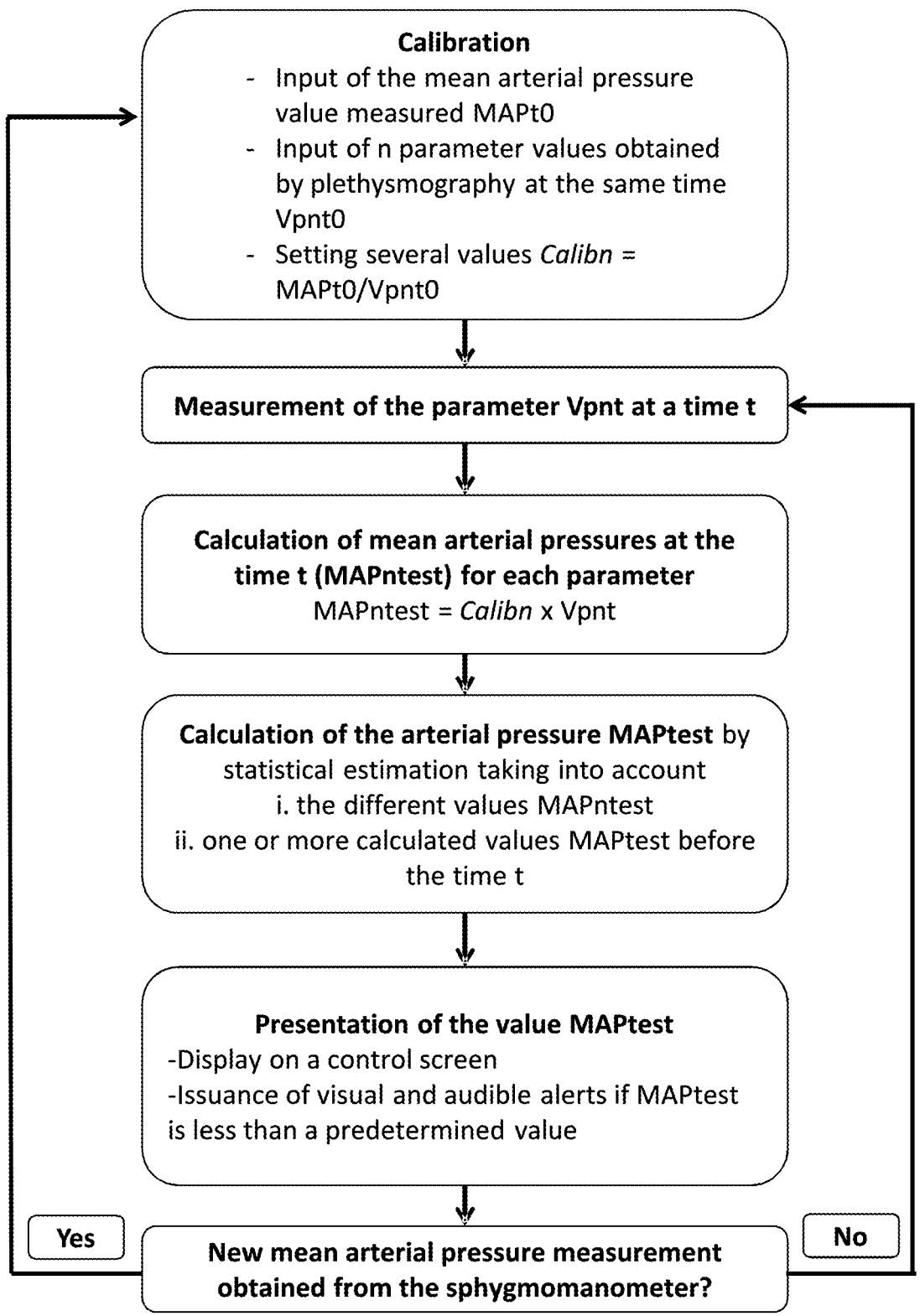
FIG. 6: Flowchart representing the implementation of another embodiment of a process according to the invention.

These values can be obtained beat-by-beat (i.e. for each pulse wave). FIG. 3 shows how these variables are measured.

Calibration also requires the mean arterial pressure (MAP) value, which can be obtained, for example, with a non-invasive pressure cuff.

A mean over several cycles (2, 3, 4, 5, 6, 8 or 10 cycles) of the value of the selected parameter can be used. This avoids disturbances such as respiratory pressure variability and irregular heart cycle. This mean is preferably the statistical median rather than the arithmetic mean.

A calibration factor Calib is estimated when taking non-invasive arterial pressure and is obtained by Calib=MAP/Vp. It is understood that the value Calib depends on the parameter chosen and that the value Calib obtained if the dicrotic wave value is chosen will be different from the value Calib if the logarithm of (the inverse of the perfusion index (PI)+1) is chosen.

Once the value Calib is obtained, the mean arterial pressure is estimated beat-by-beat using the photoplethysmographic signal as the sole data source.

The estimated MAP (MAPest) at the time t is calculated by the formula $$MAPest = Calib \times V_{Pt}, \text{ where } V_{Pt} \text{ is the value (optionally averaged) of the chosen parameter.}$$

Application Example (the Parameter being the Dicrotic Wave)

Calibration requires the values of the beat-to-beat dicrotic wave as well as intermittent values of mean arterial pressure, for example by a non-invasive pressure cuff. The dicrotic pressure value obtained by the dicrotic wave is averaged over several cycles.

The number of cycles over which the value is averaged is adjustable (for example 5 cycles). This prevents disturbances such as respiratory pressure variability and irregularities in the cardiac cycle. Averaging is done using the statistical median rather than the arithmetic mean to be more robust in the presence of noise. A calibration factor is estimated when taking non-invasive arterial pressure and is based on the current averaged dicrotic value (Pdic) and the measured mean arterial pressure (MAP). The calibration factor is obtained by Calib=MAP/Pdic.

Continuous Estimation of Mean Arterial Pressure (MAP)

Once calibration is performed, the mean arterial pressure is estimated beat-by-beat using the absorption measured by photoplethysmography as the sole signal source. The estimated MAP (MAPest) is calculated by MAPest=Calib·Pdic, where Pdic is the averaged value of the dicrotic wave value as described above.

Another Example (Use of the Perfusion Index), Especially as a Signal Quality

The PI value serves as an indicator of signal quality. Indeed, a PI value below 0.1% indicates a poor photoplethysmographic signal and can indicate to the user poor estimation quality and the more frequent need for calibration. Signal quality can usually be improved in these cases by repositioning the sensor correctly on the patient.

Incorporation into the Estimate

The PI gives information on the hemodynamic status in the mean arterial pressure in the same way as the dicrotic wave and in a complementary way. Indeed, the PI generally evolves in the opposite direction to the mean arterial pressure.

A measure referred to as mPI (for modified PI) is used and is calculated as follows: mPI=10×ln(1/PI+1). The mPI thus obtained varies in the same direction as the mean arterial pressure and the behavior is linearized with respect to the exponential behavior of PI.

A calibration Calib is performed with the measured mean arterial pressure and the mPI at the time 0 and the mean arterial pressure at the time t is calculated using MAPest=Calib×mPI(t).

Using Multiple Parameters

Several parameters can be used (dicrotic wave height, mPI, times indicated above).

One can
regularly calculate a Calib for each parameter
calculate the MAPest for each of the parameters
define the MAPest by statistical mean (Kalman filter) by weighting these values MAPest and using the value calculated at the previous time Example 3. Exemplification in Real Conditions These results were obtained on the basis of the dicrotic wave height, similar results can be obtained with the other parameters.

A study was conducted in the neurosurgical operating room or during an interventional neuroradiology procedure. Patients received the usual basic management for this type of intervention including:
Monitoring
Non-invasive hemodynamic arterial pressure monitoring by oscillometry and continuous ECG monitoring
Continuous monitoring of arterial oxygen saturation ($SpO_2$) by photoplethysmography, as well as monitoring of expired CO2.
Bispectral index (BIS) monitoring of the depth of anesthesia
Induction and maintenance of general anesthesia using target controlled infusion (TCI) including propofol and remifentanil, and curarization with atracurium besylate prior to orotracheal intubation.
All monitors were connected to a Philips monitor.

Hypotension was defined as a decrease in mean arterial pressure (MAP) of at least 20% compared with basal MAP.

In the event of hypotension, the anesthetist in charge of the patient was free to lighten the anesthesia, to administer a vascular filling or a vasoconstrictor (ephedrine 9 mg, phenylephrine 50 mcg or noradrenaline 10 mcg).

Experimental Protocol

Phase 1: Pre-Oxygenation (Baseline)—Anesthetic Induction.
Pre-oxygenation for 2 min: It is during this phase and before any injection that the basic values of all the parameters are recorded (mean of 2 values, baseline).
Remifentanil at 5 ng/mL target concentration for 1 min.
Propofol 5 µg/mL target concentration.
After the BIS has dropped below 50 and checking for absence of ciliary reflex and the patient is manually ventilatable: curarization with 0.5 mg/kg of tracrium.
Waiting time of 3 min with manual ventilation.
Phase 2: Laryngoscopy-Intubation-Manual Ventilation.
Direct laryngoscopy.
Orotracheal intubation.
Manual ventilation and probe attachment.
Phase 3: Mechanical Ventilation-Anesthesia Maintenance.
The patient is connected to the ventilator and mechanical ventilation started.
Remifentanil and propofol targets decreased to 3.5 ng/mL and 4 µg/mL, respectively.
Continuation of the collection for 3 min.
Phase 4: Possible Hypotension Correction by Vasoconstrictor.
Hypotensive episode treated with vasoconstrictor.
Continuation of the collection one minute after the vasoconstrictor takes effect.
End of collection.

During phases 1, 2 and the beginning of 3 the cuff pressure was taken every minute for an estimated mean duration of 15 minutes. The anesthetist in charge of the patient was free to deviate from the initial protocol at any time if he considered that the clinical situation required it.

Data collection was performed using Extrend data acquisition software (Ixellence), collecting signals at a frequency of 125 Hz and all numerical values.

A collection point of all the following parameters was carried out every minute:
Dicrotic wave height: the calculation of the dicrotic wave height on the plethysmography signal.
PI: the perfusion index was collected beat-by-beat.
Results:
61 patients were included in the study (median age 55 years, 32.7% males/67.3% females).
54 out of 61 patients had at least one hypotensive episode. The incidence of hypotension, defined as a decrease in MAP>20%, in the population was 88.5%. The time spent with MAP<20% is on mean 5.2 min during induction, i.e. 44% of the time.
Evolution of the Values During the Entire Induction.
The mean duration of the entire induction phase was 12±4 min.
MAP Change and Dicrotic Wave Height
MAP variations and variations in dicrotic wave height were highly correlated in a linear fashion over the induction period (see FIG. 7, especially the stability of the value Calib (FIG. 7.A)).
Analysis Based on Continuous Mean Arterial Pressure Measurement by Invasive Arterial Catheterization.

The arterial catheter is a device that allows arterial access to measure arterial pressure, invasively and continuously, and to take arterial blood samples.

Bloody arterial pressure, or invasive arterial pressure, is an invasive technique for monitoring intravascular arterial pressure through an arterial catheter.

A continuous measurement of arterial pressure was carried out by means of an arterial catheter and by the method according to the invention (calculation via the dicrotic wave height measured by plethysmography).

A perfect correlation was observed between changes in MAP measured by arterial catheter and method after the use of vasopressor drugs. The correlation was r=0.88 with 96% agreement between the variations obtained by the technique and the actual MAP measurement (FIG. 7.A).

Figure 7:
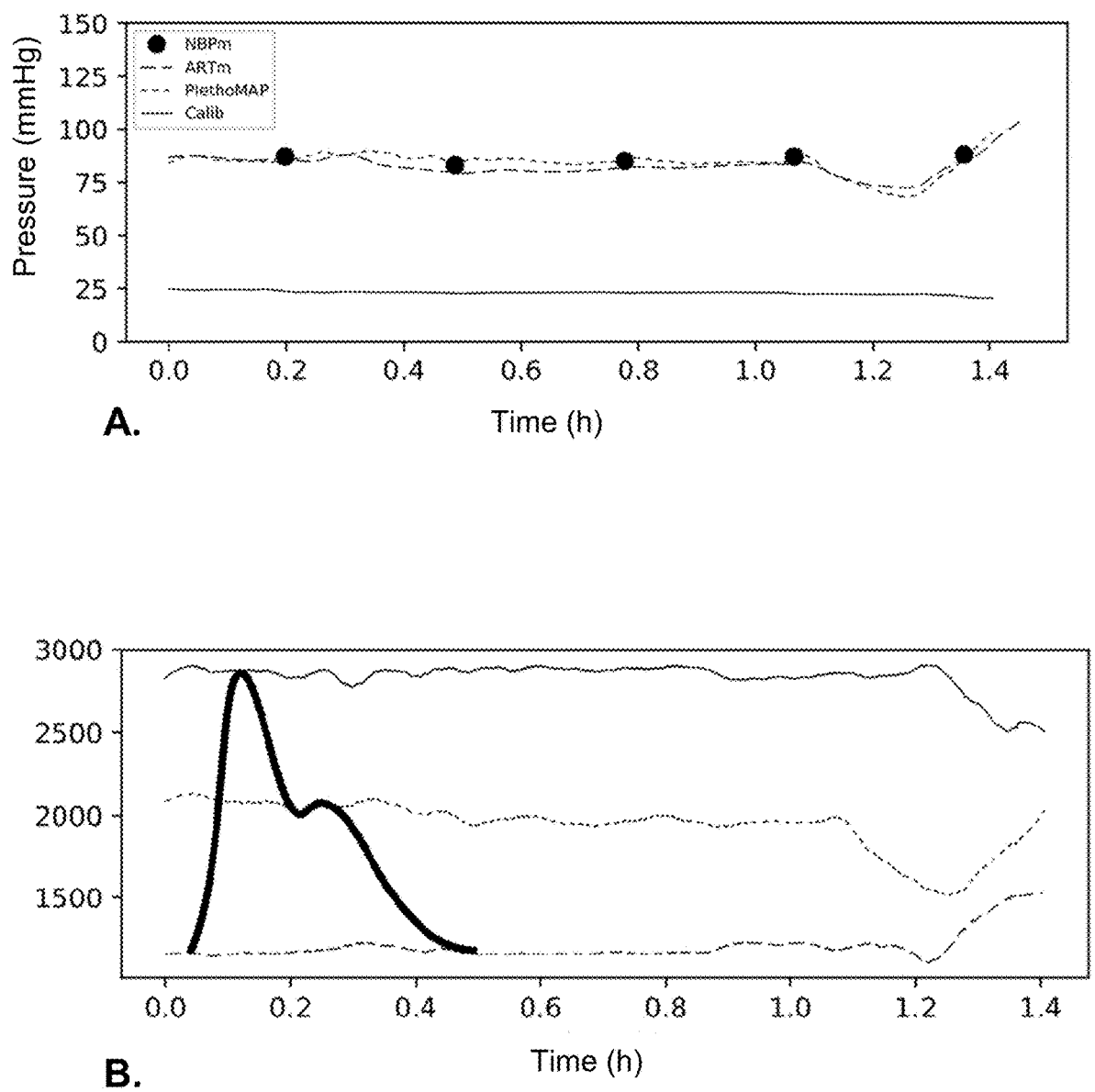
FIG. 7: A. Representation, in a representative patient, of MAP measured by an invasive method (ARTm, large dotted line), MAP estimated by a method according to the invention on the basis of the dicrotic wave height (PlethoMAP, small dotted line), MAP measured by the cuff sphygmomanometer (NBPm, black dots) and the calibration factor (Calib, solid line). B. Representation, for the same patient and the same period, of the change in the systolic peak (solid line), the dicrotic wave (small dotted line) and the diastole (large dotted line) over time. A graphical representation of the superimposed pulse wave is also shown in this figure, solely to improve understanding of the three points (what each value corresponds to). Note: the time scales of this pulse wave representation and the change in the peaks over time are different and this pulse wave representation (usually lasting 1 sec or less) is only present for information purposes.
Figure 8:
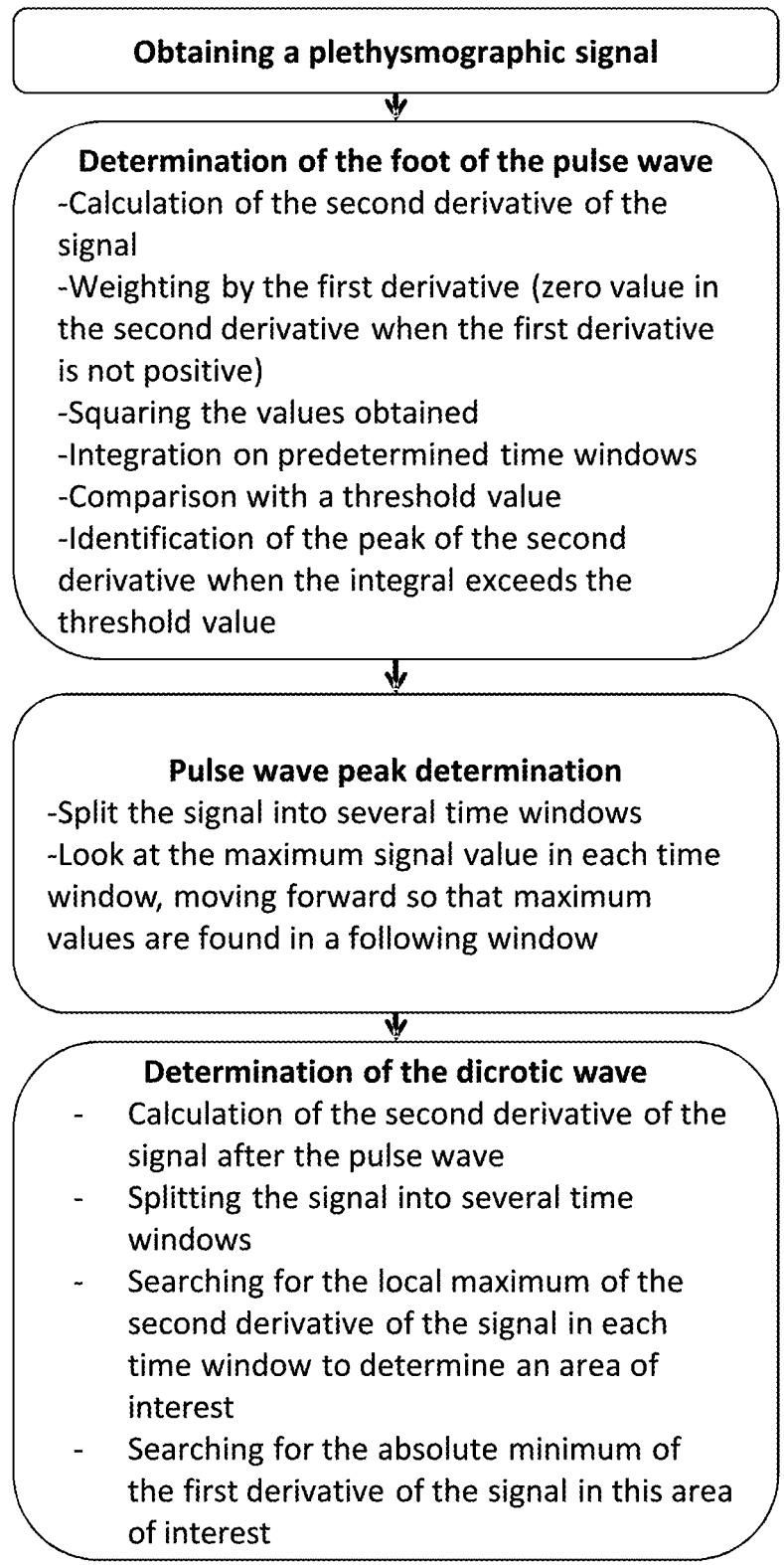
FIG. 8: Flowchart representing the implementation of an embodiment of analysis of the plethysmographic signal according to a process according to the invention.

In FIG. 7.A, a significant pressure variation can be seen at the end, which is not detected by the cuff (due to the time between two pressure measurements), but is detected by the PlethoMAP signal, thus stressing the informative nature of the method using the dicrotic wave.

In FIG. 7.B, it can be seen that only the measurement of the dicrotic wave height allows a MAP value to be obtained, and that the change in the other two parameters (systolic or diastolic value) is not sufficiently informative. It can also be seen (T=1.15 h) that the drop in dicrotic wave height is indicative of the actual drop in MAP (FIG. 7.A), whereas systolic and diastolic pressures do not vary. Therefore, the combination of these two pressures would not have detected the decrease in mean arterial pressure and would not have allowed the anesthesiologist to take any corrective action.

Example 4. Other Parameters

A study was conducted on patients in accordance with the applicable rules. The patients were over 18 years of age and underwent elective neuroradiological interventions after informed consent. The exclusion criteria for the study were cardiac arrhythmia (i.e. atrial fibrillation) and pregnancy.

Anesthesia Protocol

Prior to induction of anesthesia, standard monitoring was initiated by electrocardiogram, a non-invasive measurement of brachial ABP (PHILIPS FRANCE, Suresnes, France) set to inflate every minute, and digital pulse oximetry (PHILIPS FRANCE, Suresnes, France) placed on the second finger on the contralateral side of the ABP cuff. The bispectral index (BIS™quatro sensor, Medtronic France, Boulogne-Billancourt, France) and neuromuscular blockage monitoring (TOF Watch®, ALSEVIA PHARMA, Paris, France) were also used to monitor anesthesia. All monitoring parameters were available on a PHILIPS Intellivue MP 60 monitor (PHILIPS FRANCE, Suresnes, France). Induction of anesthesia was performed with remifentanil and propofol with an initial dose of 5 ng/mL and 5 μg/mL, respectively, and adjusted to achieve a BIS between 40 and 60. After the BIS decreased below 60 and loss of consciousness, neuromuscular blocking was performed by intravenous injection of 0.5 mg/kg of atracurium. Patients were then mechanically ventilated by tracheal intubation by direct laryngoscopy (end-tidal volume=6 mL/kg ideal body weight, positive end-tidal expiratory pressure=5 $cmH_2O$, respiration rate and oxygen fraction to achieve end-tidal $CO_2$=4.7 kPa and $O_2$ saturation >95%).

Arterial pressure was measured every minute during induction and every 5 minutes after tracheal intubation and stabilization. The patient's anesthetist may at any time change the frequency of measurements and treat 1OH episodes with fluid loading and/or vasopressors (phenylephrine and/or norepinephrine). After induction, some patients may also benefit from continuous invasive arterial pressure monitoring.

Data Collection

All parameters and monitoring curves displayed on the screen were recorded on a computer. Hemodynamic parameters (heart rate, systolic arterial pressure [SAP], mean arterial pressure [MAP] and diastolic arterial pressure [DAP]) and PPG parameters (Dicpleth, PI and $SpO_2$) were then sampled retrospectively every minute during induction. The induction period was arbitrarily set from pre-oxygenation to 3 min after connection to mechanical ventilation. Baseline values were obtained by averaging the two measurements (one minute apart) prior to the injection of anesthetics during the pre-oxygenation period. "Pre-pressor" values were defined as the pre-bolus vasopressor measurements during IOH episodes. "Peak pressure" values were defined as the maximum effects of the vasopressor bolus when the highest MAP was reached. Consistent with most studies, IOH was defined as a decrease of more than 20% from baseline MAP.

Dicpleth and PI Measurement

Figure 9:
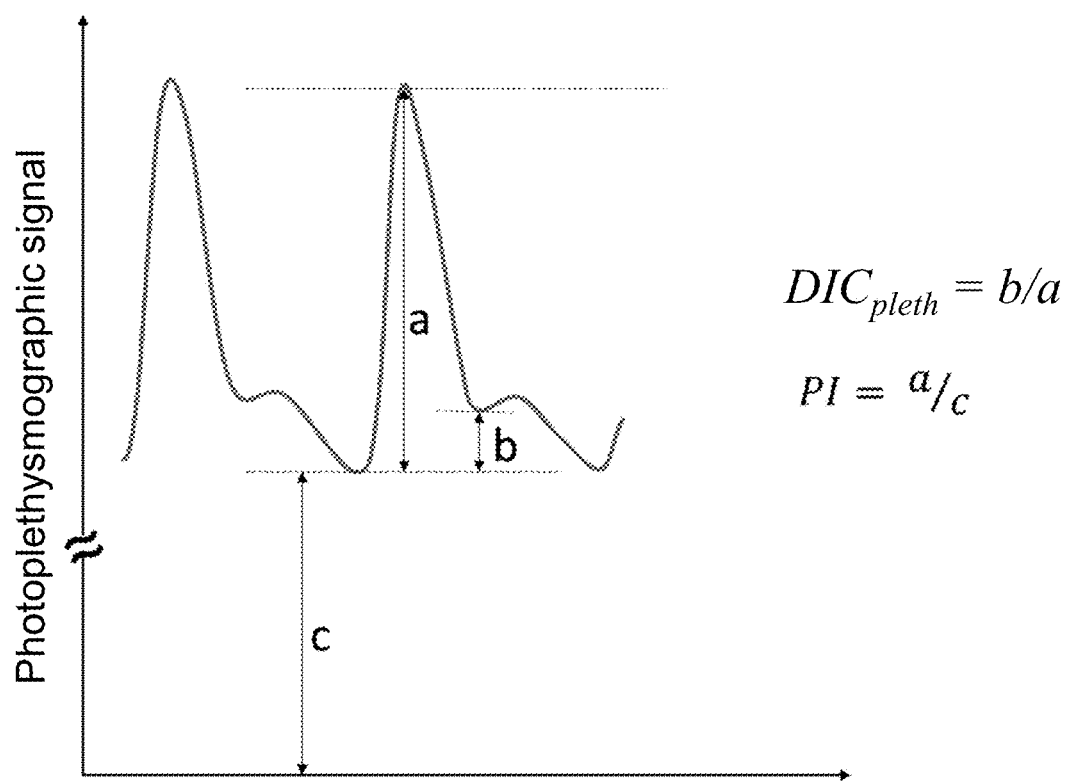
FIG. 9: Definition of Dicpleth and PI. a=amplitude of the pulsatile component of the photoplethysmographic signal (height of the systolic peak, pulsatile part); b=height of the dicrotic notch (pulsatile part); c=amplitude of the stationary component of the photoplethysmographic signal.

Dicpleth was obtained a posteriori from PPG waveforms recorded by an operator blind to ABP values. Dicpleth was defined as the ratio of the height of the dicrotic notch (from the nadir point of the complex to the notch) to the height of the systolic peak (from the same nadir point of the complex to the image), measured at the end of expiratory time in patients on mechanical ventilation (mean of 3 consecutive complexes) (FIG. 9). The PI (perfusion index) was provided by the manufacturer and is calculated as the ratio of the pulsatile component of the PPG signal to the DC component (FIG. 9).

$\Delta$MAP, $\Delta$Dicpleth and $\Delta$PI were calculated during the induction period as their relative percentage changes from their reference values. During the vasopressor boluses, variations in the respective parameters were calculated between the "pre-pressor" and "peak-pressor" measurements.

Dicradial Measurement

In patients with invasive monitoring during maintenance of anesthesia, Dicradial was also measured from the arterial pressure signal using the same methodology as Dicpleth. The last 3 heartbeats of the end of the expiratory period were used to calculate Dicradial from the height of the dicrotic notch to the height of the systolic peak. In these patients, Dicpleth, Dicradial and their relative variations ($\Delta$Dicpleth and $\Delta$Dicradial) during vasoconstrictor administration were also analyzed.

Statistical Analysis

Values were expressed as median and interquartile range [$25^{th}$ and $75^{th}$ percentiles]. Parameter changes were analyzed using the Wilcoxon ranking test. Percent agreement between the delta $\Delta$MAP, and $\Delta$Dicpleth and $\Delta$PI were calculated during the induction period. The areas under the curve (AUC) of the receiver operating characteristic (ROC) curve (with a 95% confidence interval) of $\Delta$Dicpleth and $\Delta$PI to detect IOH episodes were estimated and optionally compared using the DeLong test. The Youden method was used to determine the optimal threshold values of $\Delta$Dicpleth and $\Delta$PI for detecting IOH episodes. The combination ROC curve of $\Delta$Dicpleth and $\Delta$PI was constructed using the logistic model. Correlation tests between the two were performed using the Spearman test. $P<0.05$ was considered statistically significant. The main objective of the study was to estimate the AUC of the ROC curve of $\Delta$Dicpleth and $\Delta$PI to track IOH during induction. The sample size was determined with an expected AUC of 0.85, an expected incidence of hypotension of 80%, and a confidence interval width of 1. With a power of 80%, the number of patients to be included was then 62.16. The secondary objective was to estimate the AUC of the ROC curve (AUROC) for the combination ΔDicpleth and ΔPI. The statistical analysis was performed using Prism 6.00© (Graphpad Software, Inc, La Jolla, Calif., USA) and R 3.3.0 (R foundation for Statistical Computing, Vienna, Austria). Patients who had a non-measurable Dicpleth at baseline prior to induction of anesthesia were excluded from the analysis.

Results

From November 2014 to May 2015, 65 patients were included in the study. Prior to induction of anesthesia, Dicpleth was not measurable in 4 patients (6.2%) due to the absence of a detectable dicrotic notch on the PPG signal (class IV waveform according to Dawber et al.). Most patients had ASA II, with a mean age of 54 [39; 64] years. Hypertension, smoking and dyslipidemia were the most common comorbidities. The reason for neuroradiology procedures was mainly due to an aneurysm or an arteriovenous malformation with programmed embolization.

Change in MAP, Dicpleth and PI During the Induction Period

The median duration of induction of anesthesia was 11 [10; 13.5] minutes. A total of 720 "hemodynamic data points" were recorded: 61 at baseline and 659 after anesthetic injection, representing 659 changes from baseline.

The MAP reference value was 86 [79; 93] mmHg, giving an individual IOH limit of 69 [62; 74] mmHg. MAP decreased to 54 [48; 60] mmHg before laryngoscopy and increased to 72 [64; 82] mmHg after tracheal intubation. The mean MAP over the overall induction period was 70 [64; 71] mmHg. Fifty-four patients (88%) had at least one IOH episode during induction of anesthesia, representing 323 measurements (49% of hemodynamic points). Twenty-eight patients (46%) received a bolus of vasopressors during induction (2 phenylephrine and 26 norepinephrine).

Figure 10:
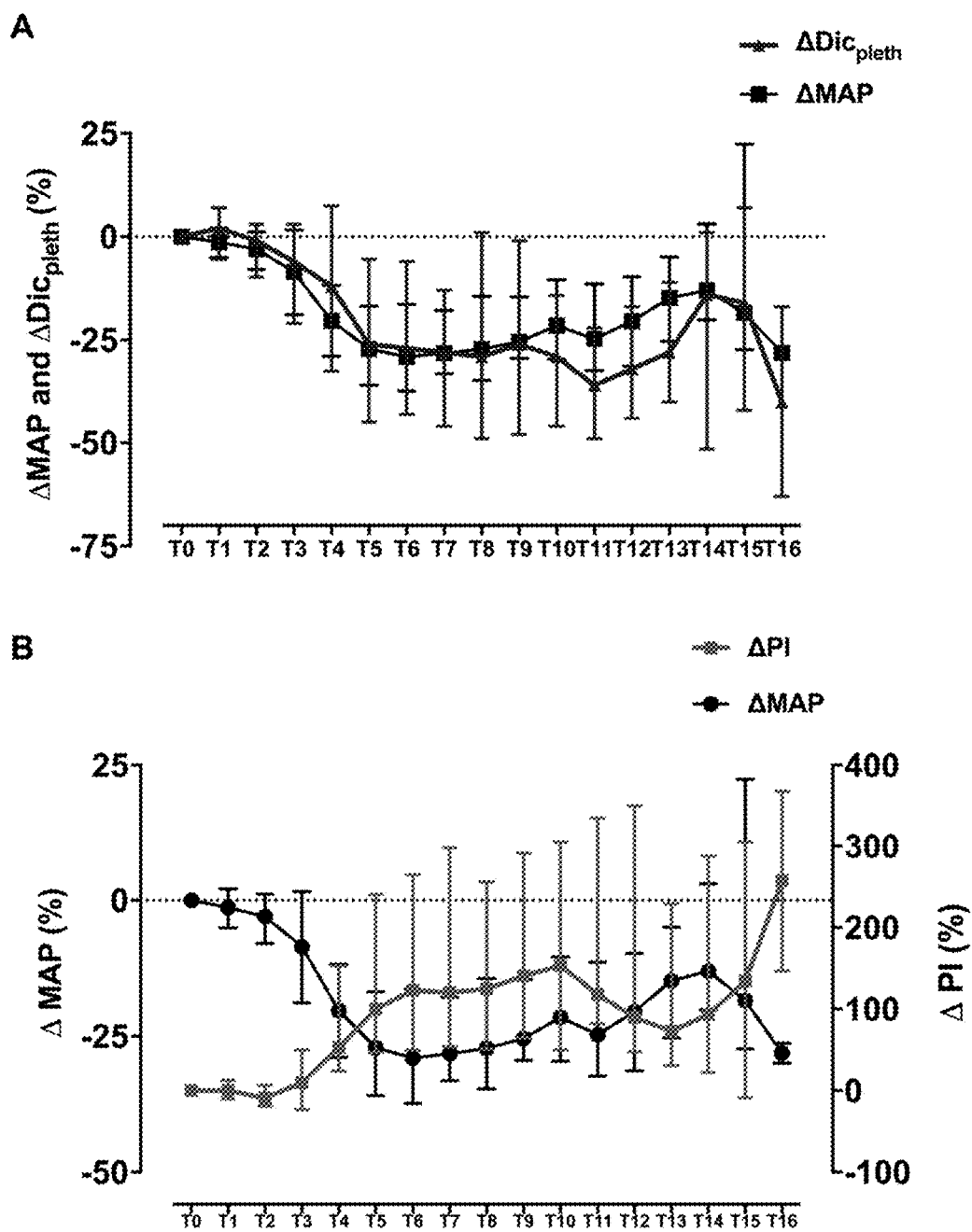
FIG. 10: Median values of ΔMAP and ΔDicpleth (A) and ΔMAP and ΔPI (B) during induction of anesthesia. ΔDicpleth: relative change in Dicpleth versus baseline; ΔPI: relative change in perfusion index versus baseline; ΔMAP: relative change in MAP versus baseline. The figure represents the change in ΔMAP and ΔDicpleth during the 16 min induction of anesthesia. The median MAP and the variation of the Dicpleth relative to the baseline are represented every minute (T "x", at "x" min from T0) from the start of induction (T0).
Figure 11:
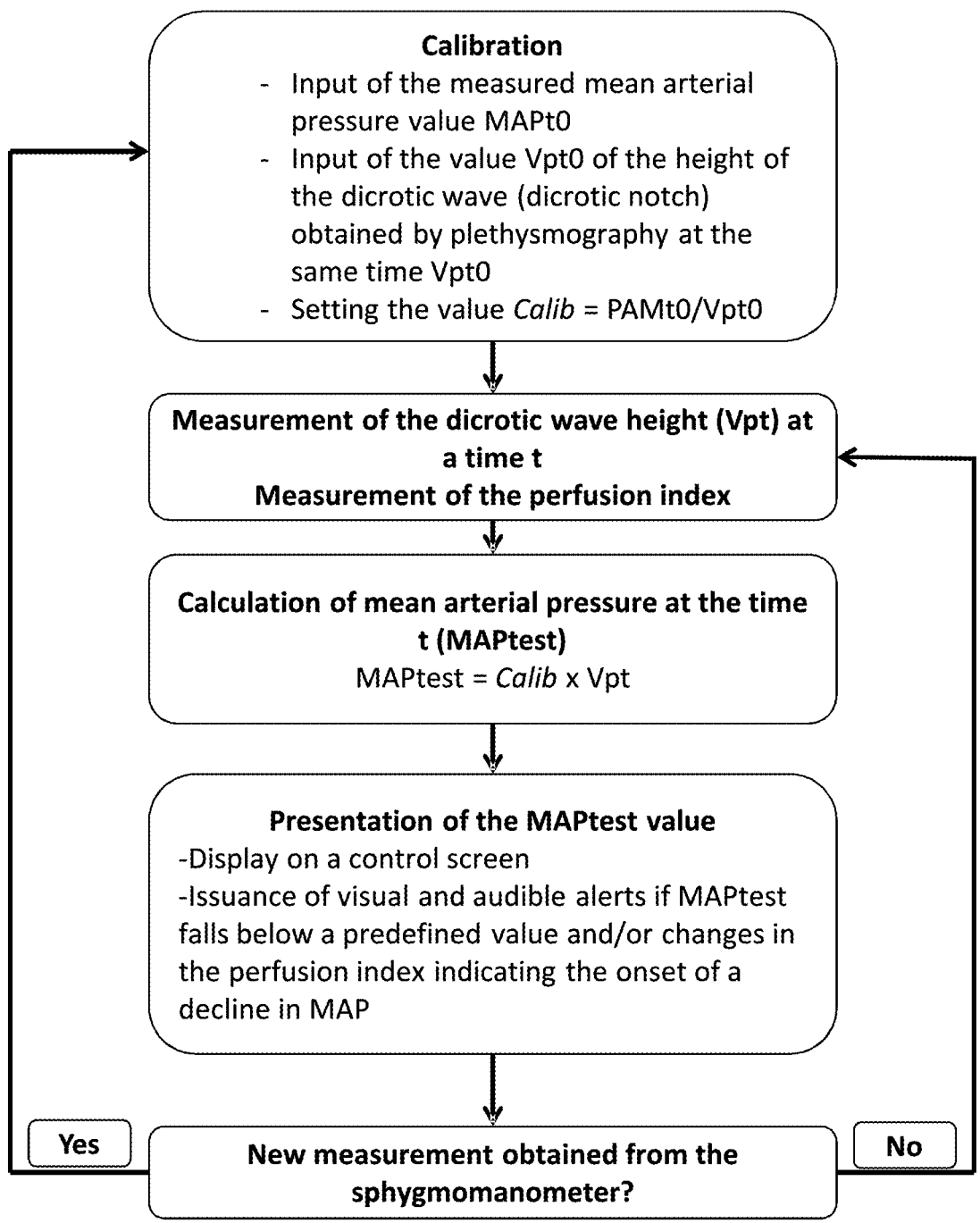
FIG. 11: Flowchart representing the implementation of a process according to the invention, using the measurement of the height of the dicrotic notch and the perfusion index.

Dicpleth was 0.54 [0.45; 0.65] at baseline, decreased to 0.36 [0.19; 0.45] (p<0.001) and increased to 0.46 [0.41; 0.56] after tracheal intubation. Baseline PI values were 1.7 [0.9; 3] and increased to 4.4 [2.8; 6.6] (p<0.001) before laryngoscopy and decreased to 3.6 [2.1; 5.4] after tracheal intubation. A visual representation of ΔMAP, ΔDicpleth and ΔPI during the induction period is described in FIG. 10. 89% agreement was found between ΔDicpleth and ΔMAP and 90% agreement between ΔPI and ΔMAP (ESM1).

Diagnostic Performance of ΔDicpleth and ΔPI for the Detection of Hypotension

The diagnostic performance values of ΔDicpleth and ΔPI are summarized in Table 1.

TABLE 1

|  | $\Delta Dic_{pleth}$ | $\Delta PI$ | $\Delta Dic_{pleth} + \Delta PI$ |
| --- | --- | --- | --- |
| AUC ROC | 0.83 95% CI 0.80-0.86 | 0.86 (95% CI 0.80-0.86) | 0.91 (95% CI 0.88-0.95) |
| P-value | <0.001 | <0.001 | <0.001 |
| Threshold value | −19% | 51% | NA |
| Sensitivity (%) | 79 | 82 | 84 |
| Specificity (%) | 84 | 74 | 84 |
| PPV (%) | 79 | 71 | 79 |
| NPV(%) | 84 | 85 | 89 |

ΔDicpleth: relative change in Dicpleth versus baseline; ΔPI: relative change in perfusion index versus baseline; AUC ROC: area under the receiving operative curve; PPV: positive predictive value; NPV: negative predictive value.

The best cut-off values from ΔDicpleth and ΔPI for IOH detection were −19% and 51%, respectively. The AUCs of ΔDicpleth and ΔPI were not significantly different (p=0.22). The combination of ΔDicpleth and ΔPI to detect episodes of intrauterine homeostasis improved detection performance with an AUC the ROC curve (0.91, (95% CI 0.88-0.95, p<0.001) statistically better than ΔDicpleth and ΔPI separately (p=0.026 and p<0.001, respectively).

Change in MAP, Dicpleth and PI During Vasoconstrictive Administration

Twenty-eight patients (46%) received a bolus of vasopressors during induction (2 phenylephrine and 26 norepinephrine). After vasopressors, DAP increased from 59 [50; 67] mmHg to 76 [68; 79] mmHg (relative change: 30% [14; 45], p<0.001). The number of people with diabetes increased from 0.34 [0.25; 0.39] to 0.48 [0.35; 0.55] (relative change: 44% [17; 63], p<0.001) and the PI decreased from 4.0 [3.3; 5.4] to 3.2 [1.8; 5.4] (relative change: −28% [−44; 13], p<0.001). ΔDicpleth and ΔPI under the effect of vasopressors were strongly related to ΔMAP (r=+0.73, 95% CI 0.48-0.87, p<0.001 and r=−0.62 95% CI −0.81 to −0.32, p<0.001; respectively).

Change in Dicpleth and Dicradial During Vasoconstrictor Administration

During maintenance of anesthesia, 48 boluses of norepinephrine were administered to 10 patients (5 [4; 6] boluses per patient) under invasive arterial pressure monitoring. Dicpleth was not measurable at 2 hemodynamic points which were excluded from the analysis. MAP increased from 70 [63; 77] mmHg to 88 [77; 98] mmHg (relative change 26% [19; 34], p<0.001). Dicpleth increased from 0.28 [0.17; 0.36] to 0.39 [0.25; 0.46] and Dicradial from 0.32 [0.21; 0.39] to 0.40 [0.31; 0.49] (relative changes 34% [20; 71], p<0.001 and 27% [14; 46], p<0.001, respectively). Dicpleth and Dicradial and their relative variations were highly correlated during vasoconstrictive administration (r=0.87 95% CI 0.83-0.90 and r=0.92 95% CI 0.85-0.95).

These results show that Dicpleth can be used as a surrogate endpoint for non-invasive and continuous MAP monitoring during induction of anesthesia. These results show a strong correlation between ΔDicpleth and ΔMAP under the action of vasoconstrictors. A 19% drop in Dicpleth had good performance in detecting IOH with a sensitivity of 79% and a specificity of 84%. PI represents the ratio between the pulsatile and continuous components of light absorption. The results show a negative correlation between ΔPI and ΔMAP under vasopressors. ΔPI was also accurate for detecting IOH, but probably a little less accurate than ΔDicpleth for providing information on IOH intensity.

The invention claimed is:

1. An ex vivo method of alerting a hypotensive state of a patient comprising the implementation of an ex vivo method for continuously evaluating the mean arterial pressure of a patient, based on values of a parameter Vp continuously calculated by plethysmography, the method comprising attaching a plethysmograph to the patient and:

I. calculating a calibration value Calib from (a) the value of the mean arterial pressure measured at a time t0, and (b) the value Vp0 linked to said parameter, measured in the patient at the time t0, wherein Calib=(value of the mean arterial pressure measured at a time t0)/Vp0 and II. calculating an estimated value MAPest of the patient's arterial pressure at a time t after t0 by the formula MAPest=Calib×Vpt, wherein Vpt is a value of a measurement of dicrotic wave height obtained at the time t, or a value averaged from a plurality of measurements obtained over a predetermined period of time, and emitting a signal when the value MAPest is below a predetermined threshold.

2. The method of claim 1, wherein the plethysmograph is attached to a finger or an earlobe of the patient and the value Vpt is obtained by photoplethysmography.

3. The method of claim 1, further comprising calculating the value of the perfusion index, the inverse of the perfusion index or the logarithm of the inverse of the perfusion index+1.

4. The method of claim 1, wherein the value Vpt is a value averaged from a plurality of measured values over a predetermined period of time.

5. The method of claim 1, further comprising recalculating the value Calib by measuring a new arterial pressure value and measuring a new value of the parameter Vp, and subsequently using the recalculated value Calib.

6. The method of claim 1, which is carried out during an entire period of a general anesthesia of the patient.

7. An ex vivo method of alerting a hypotensive state of a patient comprising the implementation of an ex vivo method for continuously evaluating the mean arterial pressure of a patient, based on values of a parameter Vp continuously calculated by plethysmography, the method comprising attaching a plethysmograph to the patient and:
   I. calculating a calibration value Calib from
      (a) the value of the mean arterial pressure measured at a time t0, and
      (b) the value Vp0 linked to said parameter, measured in the patient at the time t0, wherein Calib=(value of the mean arterial pressure measured at a time t0)/Vp0 and
   II. calculating an estimated value MAPest of the patient's arterial pressure at a time t after t0 by the formula MAPest=Calib×Vpt, wherein Vpt is a value of a measurement of dicrotic wave height obtained at the time t, or a value averaged from a plurality of measurements obtained over a predetermined period of time, and
   III. treating the patient when the estimated mean arterial pressure (MAPest) is below a predetermined threshold.

8. The ex vivo method of claim 7 wherein a vasopressor is administered to the patient.

9. The method of claim 7, wherein the plethysmograph is attached to a finger or an earlobe of the patient and the value Vpt is obtained by photoplethysmography.

10. The method of claim 7, further comprising calculating the value of the perfusion index, the inverse of the perfusion index or the logarithm of the inverse of the perfusion index+1.

11. The method of claim 7, wherein the value Vpt is a value averaged from a plurality of measured values over a predetermined period of time.

12. The method of claim 7, further comprising recalculating the value Calib by measuring a new arterial pressure value and measuring a new value of the parameter Vp, and subsequently using the recalculated value Calib.

13. The method of claim 7, which is carried out during an entire period of a general anesthesia of the patient.

* * * * *